US011779391B2

United States Patent
Govari et al.

(10) Patent No.: US 11,779,391 B2
(45) Date of Patent: Oct. 10, 2023

(54) FORMING A LESION BASED ON PRE-DETERMINED AMOUNT OF ABALTIVE ENERGY VS LESION SIZE CURVE

(71) Applicant: BIOSENSE WEBSTER (ISRAEL) LTD., Yokneam (IL)

(72) Inventors: Assaf Govari, Haifa (IL); Andres Claudio Altmann, Haifa (IL); Ella Ozeri, Binyamina (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 323 days.

(21) Appl. No.: 16/288,868

(22) Filed: Feb. 28, 2019

(65) Prior Publication Data

US 2020/0275972 A1    Sep. 3, 2020

(51) Int. Cl.
*A61B 18/00* (2006.01)
*A61B 18/14* (2006.01)

(52) U.S. Cl.
CPC .............. *A61B 18/1492* (2013.01); *A61B 2018/00351* (2013.01); *A61B 2018/00577* (2013.01);
(Continued)

(58) Field of Classification Search
CPC ........... A61B 2018/00636; A61B 2018/00642; A61B 2018/00648; A61B 2018/00654; A61B 2018/0066; A61B 2018/00666; A61B 2018/00672; A61B 2018/00678; A61B 2018/00684; A61B 2018/0069; A61B 2018/00702; A61B 2018/00708; A61B 2018/00714; A61B 2018/0072; A61B 2018/00726; A61B 2018/00732;
(Continued)

(56) References Cited

U.S. PATENT DOCUMENTS 5,868,736 A * 2/1999 Swanson ............ A61B 18/1492
606/41
5,961,513 A * 10/1999 Swanson ............ A61B 18/1492
606/41
(Continued)

FOREIGN PATENT DOCUMENTS

WO    1994010922 A1    5/1994

OTHER PUBLICATIONS

Choy Y B et al., "Lesion Size Estimator of Cardiac Radiofrequency Ablation at Different Common Locations with Different Tip Temperatures", IEEE Transactions on Biomedical Engineering, vol. 51, No. 10, Oct. 1, 2004, pp. 1859-1864.
(Continued)

*Primary Examiner* — Linda C Dvorak
*Assistant Examiner* — Nicholas S Borsch
(74) *Attorney, Agent, or Firm* — Dergosits & Noah LLP; Todd A. Noah

(57) ABSTRACT

A method of ablation includes storing in a memory a pre-determined relation between lesion size and amount of ablative energy, for each of one or more selected temperatures. Using a processor, user input is received, that indicates a lesion size and a tissue temperature. Based on the relation, an amount of energy is determined, that matches the lesion size and the tissue temperature. An ablation probe is controlled to apply the amount of ablative energy that matches the selected lesion size.

20 Claims, 2 Drawing Sheets

(52) U.S. Cl.
CPC ............ *A61B 2018/00684* (2013.01); *A61B 2018/00702* (2013.01); *A61B 2018/00714* (2013.01); *A61B 2018/00791* (2013.01); *A61B 2018/00988* (2013.01); *A61B 2218/002* (2013.01)

(58) Field of Classification Search
CPC .......... A61B 2018/00738; A61B 2018/00744; A61B 2018/0075; A61B 2018/00755; A61B 2018/00761; A61B 2018/00767; A61B 2018/00773; A61B 2018/00779; A61B 2018/00785; A61B 2018/00791; A61B 2018/00797; A61B 2018/00803; A61B 2018/00809; A61B 2018/00815; A61B 2018/00821; A61B 2018/00827; A61B 2018/00833; A61B 2018/00839; A61B 2018/00845; A61B 2018/00851; A61B 2018/00857; A61B 2018/00863; A61B 2018/00869; A61B 2018/00875; A61B 2018/0088; A61B 2018/00886; A61B 2018/00892; A61B 18/1492; A61B 2018/00351; A61B 2018/00577; A61B 2018/00988; A61B 2218/002; A61B 2090/061; A61B 2034/101; A61B 34/10; A61B 18/12; A61B 2018/00029; A61B 5/74; A61B 5/742; A61B 5/7425; A61B 5/743; A61B 5/7435

See application file for complete search history.

(56) References Cited

U.S. PATENT DOCUMENTS

| | | | | |
|---|---|---|---|---|
| 6,056,745 | A  * | 5/2000  | Panescu  | A61B 18/00 606/41 |
| 6,358,245 | B1 * | 3/2002  | Edwards  | A61B 18/1477 606/42 |
| 6,409,722 | B1 * | 6/2002  | Hoey     | A61B 18/18 606/41 |
| 9,844,406 | B2 * | 12/2017 | Edwards  | A61B 18/1206 |
| 2011/0144524 | A1 | 6/2011 | Fish et al. | |
| 2014/0046316 | A1 * | 2/2014 | Ladtkow | A61B 10/0233 606/33 |
| 2014/0194869 | A1 | 7/2014 | Leo et al. | |
| 2014/0243813 | A1 | 8/2014 | Paul et al. | |
| 2014/0276783 | A1 * | 9/2014 | Srivastava | A61N 1/403 606/41 |
| 2017/0014181 | A1 | 1/2017 | Bar-Tal et al. | |
| 2019/0046257 | A1 * | 2/2019 | Vilims | A61B 34/10 |

OTHER PUBLICATIONS

European Search Report for corresponding EPA No. 20159744.0 dated Jul. 20, 2020.

* cited by examiner

FORMING A LESION BASED ON PRE-DETERMINED AMOUNT OF ABALTIVE ENERGY VS LESION SIZE CURVE

FIELD OF THE INVENTION

The present invention relates generally to radiofrequency (RF) ablation, and particularly to cardiac RF ablation.

BACKGROUND OF THE INVENTION

Various techniques for planning RF ablation were proposed in the patent literature. For example, U.S. Patent Application Publication 2011/0144524 describes a system for displaying characteristics of target tissue during an ablation procedure. The system includes an electronic control unit (ECU) configured to receive data regarding electrical properties of the target tissue for a time period. The ECU is also configured to determine values responsive to the data and indicative of at least one of a predicted depth of a lesion in the target tissue, a predicted temperature of the target tissue, and a likelihood of steam pop of the target tissue for the time period. The system further includes a display device configured to receive the values and display a visual representation the respective indicative parameters listed above.

As another example, U.S. Patent Application Publication 2014/0243813 describes ablation systems and methods for providing feedback on lesion formation in real-time. The methods and systems assess absorptivity of tissue based on a degree of electric coupling or contact between an ablation electrode and the tissue. The absorptivity can then be used, along with other information, including, power levels and activation times, to provide real-time feedback on the lesions being created. Feedback may be provided, for example, in the form of estimated lesion volumes and other lesion characteristics. The methods and systems can provide estimated treatment times to achieve a desired lesion characteristic for a given degree of physical contact, as well as depth of a lesion being created.

U.S. Patent Application Publication 2014/0194869 describes a method and apparatus that utilizes a force-time integral for real time estimation of lesion size in catheter-based ablation systems. The apparatus measures the force exerted by a contact ablation probe on a target tissue and integrates the force over an energization time of the ablation probe. The force-time integral can be calculated and utilized to provide an estimated lesion size (depth, volume and/or area) in real time. The force-time integral may also account for variations in the power delivered to the target tissue in real time to provide an improved estimation of the lesion size. In one embodiment, the force metric can be used as feedback to establish a desired power level delivered to the probe to prevent steam popping.

U.S. Patent Application Publication 2017/014181 describes a method, consisting of ablating tissue for a time period, measuring a contact force applied during the time period, and measuring a power used during the time period. The method further includes ceasing ablating the tissue when a desired size of a lesion produced in the tissue, as estimated using an integral over the time period of a product of the contact force raised to a first non-unity exponent and the power raised to a second non-unity exponent, is reached.

SUMMARY OF THE INVENTION

An embodiment of the present invention provides a method of ablation, including storing in a memory a pre-determined relation between lesion size and amount of ablative energy, for each of one or more selected temperatures. Using a processor, user input is received, that indicates a lesion size and a tissue temperature. Based on the relation, an amount of energy is determined, that matches the lesion size and the tissue temperature. An ablation probe is controlled to apply the amount of ablative energy that matches the selected lesion size.

In some embodiments, the selected tissue temperature includes a temperature of an ablative electrode that applies the ablative energy.

In some embodiments, the method further includes presenting to the user the indicated lesion size and tissue temperature, and the determined amount of energy.

In an embodiment, determining the amount of energy includes reading at least part of the relation from a lookup table.

There is additionally provided, in accordance with an embodiment of the present invention, a system for ablation, including a memory and a processor. The memory is configured to store a pre-determined relation between lesion size and amount of ablative energy, for each of one or more selected temperatures. The processor is configured to receive user input indicating a lesion size and a tissue temperature, to determine, based on the relation, an amount of energy that matches the lesion size and the tissue temperature, and to control an ablation probe to apply the amount of ablative energy that matches the selected lesion size.

The present invention will be more fully understood from the following detailed description of the embodiments thereof, taken together with the drawings in which:

DETAILED DESCRIPTION OF EMBODIMENTS

Overview

Figure 1:
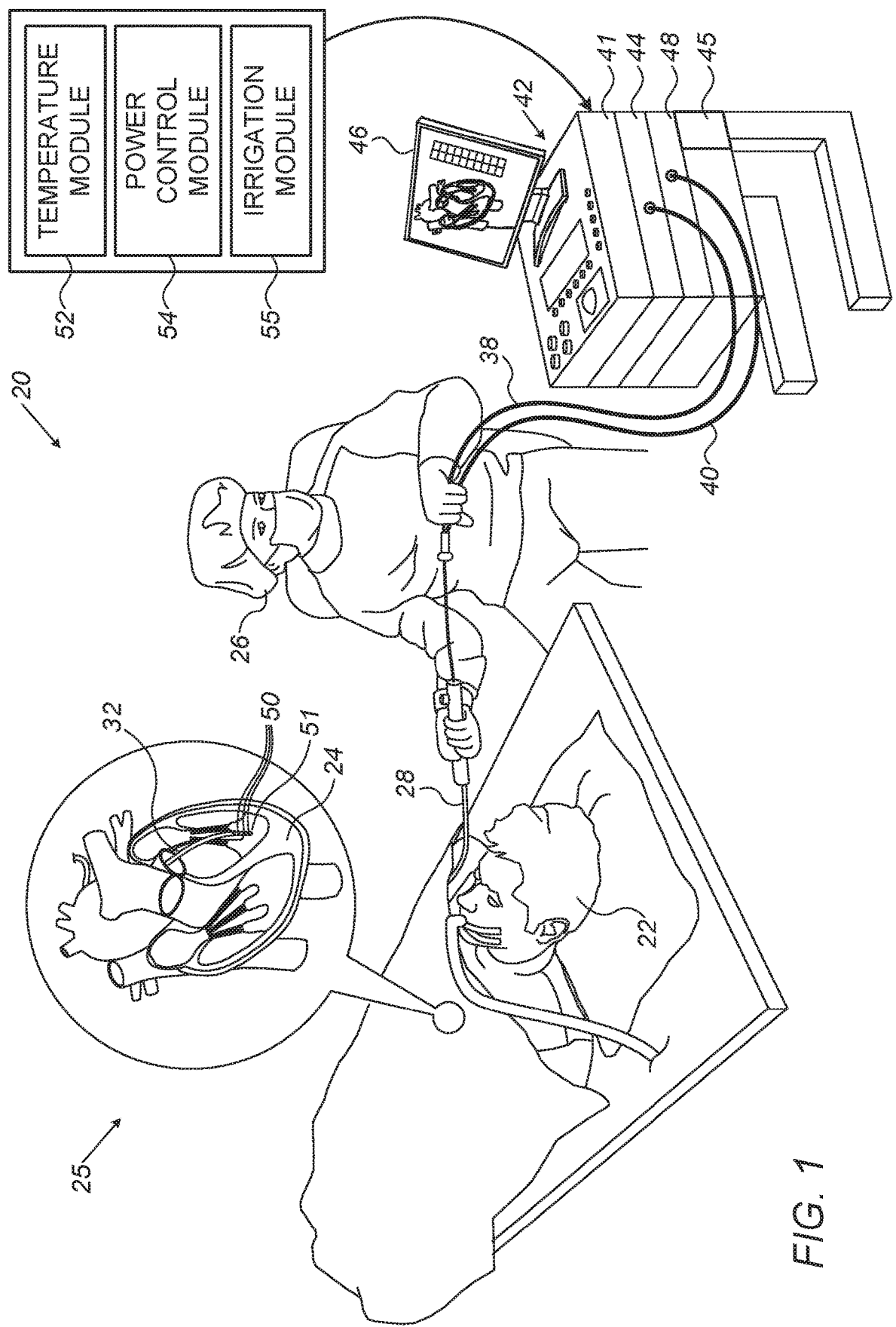
FIG. 1 is a schematic, pictorial illustration of a system for cardiac radiofrequency (RF) ablation therapy, in accordance with an embodiment of the present invention.

A treatment of arrhythmia may include ablating a lesion in cardiac tissue using a source of thermal energy (e.g., by heating tissue). The clinical efficacy of the lesion largely depends on the depth of the lesion, which is governed by the amount of effective (e.g., useful) ablative energy deposited in tissue where the lesion is formed.

However, the effective ablative energy cannot be accurately estimated, as it depends, for example, on unknown tissue properties such as fat content. Therefore, for a given energy output of a generator, such as a radiofrequency (RF) generator, the resulting effective RF energy may be too low or too high. Low effective ablative energy may result in creating an insufficiently deep lesion, whereas an excessively high effective ablative energy may cause side effects such as steam-pops (e.g., due to very high tissue temperature), and side effects such as tissue perforation and collateral damage.

Tissue temperature during ablation is indeed considered indicative of the effective RF energy deposited, where a higher temperature predicts the formation of a deeper lesion.

Thus, predetermining a target tissue temperature to be maintained during ablation may assist in achieving both target lesion depth and avoiding side effects, such as those listed above.

Embodiments of the present invention that are described hereinafter provide a method for accurately predetermining and controlling both tissue temperature and lesion size (e.g., lesion depth) during thermal ablation, such as (RF) ablation. The disclosed method comprises planning the ablation in an energy mode, wherein, in order to meet both targets of lesion depth and tissue temperature, a processor selects, using a pre-determined relation between lesion depth and output energy at different constant temperatures, a corresponding amount of ablating RF energy to apply to tissue.

The disclosed pre-determined relation may be derived from a model and/or be based on calibration. For example, such a relation may be pre-measured in vitro (and/or using an animal model) and stored in a memory of the ablation system. Using the pre-determined relation, the disclosed method enables a processor to plan an ablation based only on two measured parameters (energy output of a generator and tissue temperature).

For example, in an embodiment, a physician selects (a) target lesion depth, and (b) tissue temperature during ablation to be, by example, 50° C., a low enough temperature at which it is known that side effects such as steam-pops do not occur in tissue. The processor that the physician operates then extracts the disclosed pre-determined relation between lesion depth and amount of ablative energy at the selected temperature, which can be in a form of a lookup table, and determines from the relation the amount of ablative energy required for achieving the selected lesion depth at the selected temperature.

In a subsequent ablation procedure, based on the selection, an ablation system applies an algorithm, as described below, in which the processor controls an ablation probe to apply the amount of ablative energy that matches the selected lesion size. In an embodiment, the processor may use one or two additional control parameters, such as irrigation flow rate, rather than attempting to control multiple parameters, which might include, for example, instantaneous RF power and force of contact. In an embodiment, the processor is configured to operate the algorithm to determine if the ablation is proceeding as planned, and to control the ablation based on feedback from readings of the two measured parameters (i.e., energy output of the generator and tissue temperature) In some embodiments, if the level of RF power applied is lowered by the processor, for example, in order to meet target tissue temperature, the processor is configured to extend the ablation time so that the selected amount of ablating RF energy is fully delivered, so as to achieve target lesion depth.

The described RF ablation planning technique, using the disclosed pre-determined relation, may enable achieving target lesion depth while maintaining tissue temperature, and therefore may improve the efficacy and safety of a catheter-based RF ablation procedure.

System Description

FIG. 1 is a schematic, pictorial illustration of a system 12 for cardiac radiofrequency (RF) ablation therapy, in accordance with an embodiment of the present invention. Typically, a memory 45 of system 20 stores numerous ablation protocols for different clinical scenarios, such as the protocol described in FIG. 2.

A physician 26 inserts a catheter 28 through a blood vessel into a chamber of a heart 24 of a subject 22, and manipulates the catheter so that a distal end 32 of the catheter contacts the endocardium in an area that is to be treated. A tip electrode 51 of catheter 28, seen in inset 25, comprises one or more temperature sensors 50.

After positioning distal end 32 at an ablation site, and ensuring that the tip is in contact with the endocardium, operator 26 actuates an RF energy generator 44 in a control console 42 to supply RF energy via a cable 38 to distal end 32. Meanwhile, an irrigation pump 48 supplies a cooling fluid, such as normal saline solution, via a tube 40 and a lumen in catheter 28 to the distal end. Typically, both before and during the ablation, a display 46 displays those values of the ablation parameters, such as listed in Tables I-IV below, to physician 26.

Operation of the RF energy generator and the irrigation pump may be coordinated in order to give the appropriate volume of irrigation during ablation, so as to cool the tip of the catheter and the tissue without overloading the heart with irrigation fluid. Each temperature sensor inside temperature sensors 50 provides feedback to console 42 for use, for example, in controlling the RF power and/or irrigation flow rate to maintain a given tissue-temperature.

In order to operate system 12, a processor 41 includes a number of modules used by the processor to operate the system. These modules comprise a temperature module 52, a power control module 54, and an irrigation module 55, the functions of which are described below. In particular, processor 41 runs a dedicated algorithm as disclosed herein, included in FIG. 3, that enables processor 41 to perform the disclosed steps, as further described below.

Although the pictured embodiment relates specifically to the use of a tip ablation device for ablation of heart tissue, the methods described herein may alternatively be applied in ablation devices comprising multiple ablation electrodes, when the operation of each electrode is independently controlled by processor 41.

Figure 2:
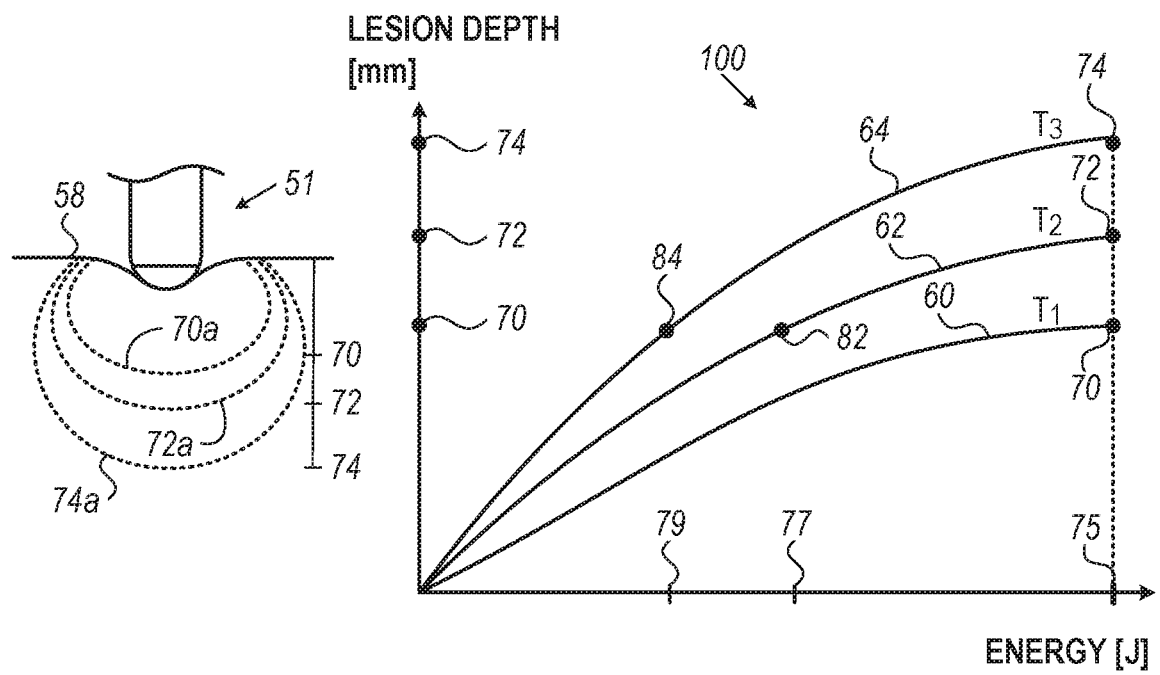
FIG. 2 is a graph schematically showing a pre-determined relation between lesion size and RF ablative energy at different constant temperatures, in accordance with an embodiment of the present invention.

Forming a Lesion Based on Pre-Determined Amount of Abaltive Energy Vs. Lesion Size Curve FIG. 2 is a graph schematically showing a pre-determined relation 100 between lesion size and RF ablative energy at different constant temperatures, in accordance with an embodiment of the present invention. As seen, relation 100 comprises a set of curves 60-64, where each curve gives an expected lesion depth as a function of generator 44 output RF energy, and at three different constant tissue temperatures $T_1 < T_2 < T_3$, respectively.

For example, at an output energy level 75, temperature $T_1$ corresponds to lesion depth 70, $T_2$ corresponds to lesion depth 72, and $T_3$ corresponds to lesion depth 74. Thus, maintaining lower tissue temperature during ablation results in a shallower lesion.

As further seen in FIG. 2, not only different temperatures $T_1$, $T_2$ and, $T_3$ correspond to tissue depths 70, 72 and 74, respectively, but also overall different lesion sizes (e.g., volumes) 70a, 72a, and 74a, respectively.

In some cases, for example if the risk of steam-pops is less significant, a user may select achieving the same lesion depth from different temperature curves. Such a selection amounts to using a different amount of effective ablative energy with each temperature, based on the disclosed relation.

This is seen by ablative energies 75, 77, and 79, which all produce the same lesion depth, indicated on curves 60-64 by points 70, 82, and 84, respectively.

An ablation method in an energy mode, which may vary RF power and irrigation flow rate (and, contrary to the herein disclosed technique allows also temperature to vary) is described in a U.S. patent application entitled "Energy-Guided Radiofrequency (RF) Ablation,", which is assigned to the assignee of the present patent application and whose disclosure is incorporated herein by reference.

Finally, tissue temperature may be affected by the effective energy that electrode 51 passes through tissue surface 58. The effectivity of electrode 51 in passing energy directly to tissue beneath it may depend on the contact force that electrode 51 exerts on tissue surface 58.

Figure 3:
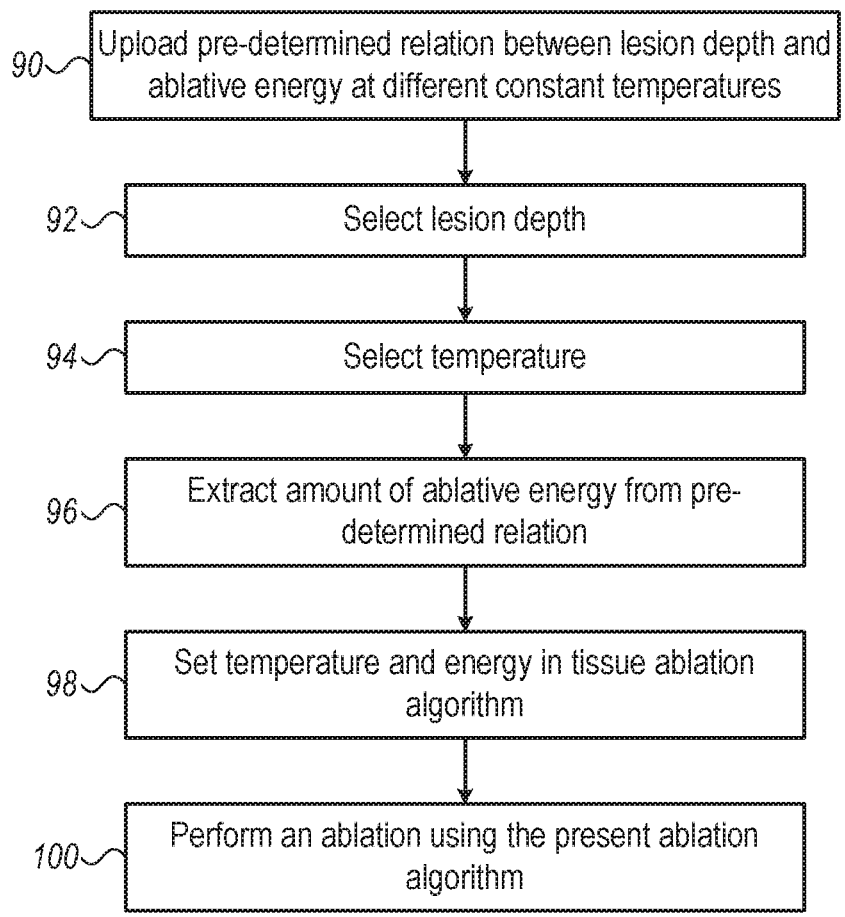
FIG. 3 is a flow chart that schematically illustrates a method for planning RF ablation using the relation of FIG. 2, according to an embodiment of the present invention.

FIG. 3 is a flow chart that schematically illustrates a method for planning RF ablation using the curves of FIG. 2, according to an embodiment of the present invention. The process begins by physician 26 uploading pre-determined relation 100 comprising lesion depth as a function of ablative energy, such as curves 60-64, at a pre-determined relation uploading step 90. Next, physician 26 selects lesion depth, at a lesion depth selection step 92. Physician 26 further selects target tissue temperature at tissue temperature selection step 94. Based on steps 90-94, processor 41, operated by physician 26, extracts the required energy using the disclosed relation (e.g., stored lookup table), at an energy selection step 96. The physician then sets the selections into system 20 using a user interface, as inputs for an ablation algorithm applied by system 20, at a parameter setting step 98.

In some embodiments, the processor presents the above selections in one of Tables I-IV, for example on a display of system 20. Typically, the allowed range of power and irrigation flowrate are automatically set by the system.

Tables I-IV provide four different settings that may be used for optimizing lesion depth while minimizing collateral damage, depending on the clinical need:

Table I— Low depth
Table II— Medium depth
Table III— High depth
Table IV— Extra high depth Low Depth Parameters:

TABLE I

| Parameter | Range |
| --- | --- |
| Preset ablative energy | 270 J |
| Maximum power level | 90 W |
| Power range | 0-90 W |
| Allowable temperature range | 45-65° C. (typically 50° C.) |
| Allowable irrigation flow rate | 4-25 ml/min (this is mainly depending on the catheter design. (Typically, 4-15 ml/min) |
| Maximal ablation time | 3-6 Sec (Typically 4 sec) |

Medium Depth Parameters

TABLE II

| Parameter | Range |
| --- | --- |
| Preset ablative energy | 360 J |
| Maximum power level | 90 W |
| Power range | 0-90 W |

TABLE II-continued

| Parameter | Range |
| --- | --- |
| Allowable temperature range | 45-65° C. (typically 50° C.) |
| Allowable irrigation flow rate | 4-25 ml/min (mainly depending on the catheter design. (Typically, 4-15 ml/min) |
| Maximal ablation time | 4-8 Sec (Typically 6 sec) |

High Depth Parameters:

TABLE III

| Parameter | Range |
| --- | --- |
| Preset ablative energy | 560 J |
| Maximum power level | 70-90 W (Typically 70 W) |
| Power range | 0-90 W |
| Allowable temperature range | 45-65° C. (typically 50° C.) |
| Allowable irrigation flow rate | 4-25 ml/min (mainly depending on the catheter design. (Typically, 4-15 ml/min) |
| Maximal ablation time | 6-12 Sec (Typically 10 sec) |

Extra High Depth Parameters:

TABLE IV

| Parameter | Range |
| --- | --- |
| Preset ablative energy | 1500-3000 J |
| Maximum power level | 50 W |
| Power range | 0-50 W |
| Allowable temperature range | 40-55° C. (typically 45° C.) |
| Allowable irrigation flow rate | 4-25 ml/min (mainly depending on the catheter design. Typically, 4-15 ml/min) |
| Maximal ablation time | 30-90 Sec (Typically 60 sec) |

Relation uploading step 90 is implemented before physician 26 performs an ablation.

At a subsequent ablation session 100, system 20 uses the selected parameters based on the disclosed relation (e.g., curves 60-64 that may be provided as a lookup table) to achieve the required lesion depth while maintaining target tissue temperature.

A display of system 20 may be further configured to display to physician 26, by methods which are known in the art, the progress of the RF delivery to the electrode.

The example flow chart shown in FIG. 3 is chosen purely for the sake of conceptual clarity. The present embodiment also comprises additional steps of the algorithm, such as checking a level of contact force of electrode 51 with tissue. In an embodiment, during the subsequent ablation procedure, a processor that applies the disclosed planning method is configured to monitor actual tissue temperature to maintain the temperature within a given tolerance. During the ablation, both irrigation flow rate and the level of RF power output may be automatically adjusted by the processor in order to maintain tissue temperature within the given tolerance.

Although the embodiments described herein mainly address cardiac applications, the methods and systems described herein can also be used, for example, in planning an ablation of other organs of the body.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method of ablation, comprising:
   receiving, by a processor of a computing system, a user input indicating a target lesion size in tissue and a target tissue temperature to be maintained during ablation;
   determining by the processor, based solely on: i) a pre-determined relation between lesion size and an amount of ablative energy required to maintain a constant tissue temperature during ablation, and ii) the inputted target lesion size and the inputted target tissue temperature, an amount of ablative energy required to be applied to the tissue by at least one electrode for achieving the inputted target lesion size at the inputted target tissue temperature, the pre-determined relation being one of a plurality of pre-determined relations between lesion size and ablative energy required to maintain tissue temperature corresponding to a plurality of tissue temperatures, the plurality of pre-determined relations being derived from at least one of a model or through calibration and stored in a memory accessible by the computing system; and
   controlling an ablation probe to apply the amount of ablative energy by the at least one electrode for the inputted lesion size and inputted target tissue temperature based solely on the pre-determined relationship between lesion size and tissue temperature stored in the memory accessible by the computing system.

2. The method according to claim 1, wherein the selected tissue temperature comprises a temperature of an ablative electrode that applies the ablative energy.

3. The method according to claim 1 further comprising presenting to the user the indicated lesion size and tissue temperature, and the determined amount of energy.

4. The method according to claim 1, wherein determining the amount of energy comprises reading at least part of the relation from a lookup table.

5. The method according to claim 1, further comprising detecting a level of contact force of the at least one electrode to determine the effectivity of the at least one electrode in passing energy to the tissue.

6. The method according to claim 1 further comprising monitoring the temperature of the tissue during the ablation to maintain the temperature within a predetermined tolerance range.

7. The method according to claim 6 further comprising adjusting an irrigation flow rate and the level of power output to maintain the temperature within the predetermined tolerance range.

8. A system for ablation, the system comprising:
   one or more processors of a computing system; and
   a non-transitory computer readable medium storing a plurality of instructions, which when executed, cause the one or more processors to:
   receive, by the one or more processors, user input indicating a target lesion size in tissue and a target tissue temperature to be maintained during ablation;
   determine by the one or more processors, based solely on: i) a pre-determined relation between lesion size and an amount of ablative energy required to maintain a constant tissue temperature during ablation, and ii) the inputted target lesion size and the inputted target tissue temperature, an amount of ablative energy required to be applied to the tissue by at least one electrode for achieving the inputted target lesion size at the inputted target tissue temperature, the pre-determined relation being one of a plurality of pre-determined relations between lesion size and ablative energy required to maintain tissue temperature corresponding to a plurality of tissue temperatures, the plurality of pre-determined relations being derived from at least one of a model or through calibration and stored in a memory accessible by the computing system; and
   control an ablation probe to apply the amount of ablative energy by the at least one electrode for the inputted lesion size and inputted target tissue temperature based solely on the pre-determined relationship between lesion size and tissue temperature stored in the memory accessible by the computing system.

9. The system according to claim 8, wherein the selected tissue temperature comprises a temperature of an ablative electrode that applies the ablative energy.

10. The system according to claim 8, wherein the processor is further configured to present to a user the indicated lesion size and tissue temperature, and the determined amount of energy.

11. The system according to claim 8, wherein the pre-determined relation is stored in a lookup table.

12. The system according to claim 8, wherein the program instructions further cause the one or more processors to detect a level of contact force of the at least one electrode to determine the effectivity of the at least one electrode in passing energy to the tissue.

13. The system according to claim 8, wherein the program instructions further cause the one or more processors to monitor the temperature of the tissue during the ablation to maintain the temperature within a predetermined tolerance range.

14. The system according to claim 13, wherein the program instructions further cause the one or more processors to adjust an irrigation flow rate and the level of power output to maintain the temperature within the predetermined tolerance range.

15. A computer program product comprising computer-readable program code to be executed by one or more processors of a computing system when retrieved from a non-transitory computer-readable medium, the program code including instructions to:
   receive a user input indicating only a target lesion size in tissue and a target tissue temperature to be maintained during ablation;
   determine, based solely on: i) a pre-determined relation between lesion size and an amount of ablative energy required to maintain a constant tissue temperature during ablation, and ii) the inputted target lesion size and the inputted target tissue temperature, an amount of ablative energy required to be applied to the tissue by at least one electrode for achieving the inputted target lesion size at the inputted target tissue temperature, the pre-determined relation being one of a plurality of pre-determined relations between lesion size and ablative energy required to maintain tissue temperature corresponding to a plurality of tissue temperatures, the plurality of pre-determined relations being derived from at least one of a model or through calibration and stored in a memory accessible by the computing system; and control an ablation probe to apply the amount of ablative energy by the at least one electrode for the inputted lesion size and inputted target tissue temperature based solely on the pre-determined relationship between lesion size and tissue temperature stored in the memory accessible by the computing system.

16. The computer program product according to claim 15, wherein the selected tissue temperature comprises a temperature of an ablative electrode that applies the ablative energy.

17. The computer program product according to claim 15, wherein the program code further includes instructions to present to the user the indicated lesion size and tissue temperature, and the determined amount of energy.

18. The computer program product according to claim 15, wherein determining the amount of energy comprises reading at least part of the relation from a lookup table.

19. The computer program product according to claim 15 wherein the program instructions further cause the one or more processors to detect a level of contact force of the at least one electrode to determine the effectivity of the at least one electrode in passing energy to the tissue.

20. The computer program product according to claim 15 wherein the program instructions further cause the one or more processors to monitor the temperature of the tissue during the ablation to maintain the temperature within a predetermined tolerance range, wherein maintaining the temperature within a predetermined tolerance range comprises adjusting an irrigation flow rate and the level of power output.

* * * * *